United States Patent [19]

Meilland, deceased

[11] Patent Number: Plant 7,277

[45] Date of Patent: Jul. 24, 1990

[54] ROSE PLANT-MEITONJE VARIETY

[75] Inventor: Marie-Louise Meilland, deceased, late of Antibes, France, by Jean-Pierre le Naour, legal representative

[73] Assignee: The Conard-Pyle Company, West Grove, Pa.

[21] Appl. No.: 321,144

[22] Filed: Mar. 9, 1989

[51] Int. Cl.[5] ..... A01H 5/00

[52] U.S. Cl. ..... Plt./9

[58] Field of Search ..... Plt./9, 7

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which forms abundantly and continuously highly attractive fully double blossoms. The blossoms are carmine rose in coloration. The plant exhibits a vigorous, compact and bushy growth habit, and is not particularly affected by cryptogamic diseases.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Meilucca variety (non-patented in the United States). The Meilucca variety is sometimes known as the Darling Flame variety. The male parent (i.e., the pollen parent) of the new variety was the Meifinaro variety (U.S. Plant Pat. No. 5,180). The parentage of the new variety can be summarized as follows:

Meilucca × Meifinaro.

The seeds resulting from the above pollination were sown and 1,563 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive fully double blossoms which are carmine rose in coloration,
(b) exhibits a vigorous, compact and bushy growth habit, and
(c) is not particularly affected by cryptogamic diseases.

The new variety well meets the needs of the horticultural industry for many usages. It is particularly well-suited for use as attractive ornamentation in parks and gardens.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meitonje variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were observed during September while budded on *Rosa froebelli* understock and growing outdoors at LeCannet-des-Maures, Var, France.

FIG. 13 illustrates a specimen of a main branch;

DETAILED DESCRIPTION

Figures 1, 2, 3, 4, 5, 6, 7, 8, 9, 10, 11, 12, 14, 15, 16, 17:
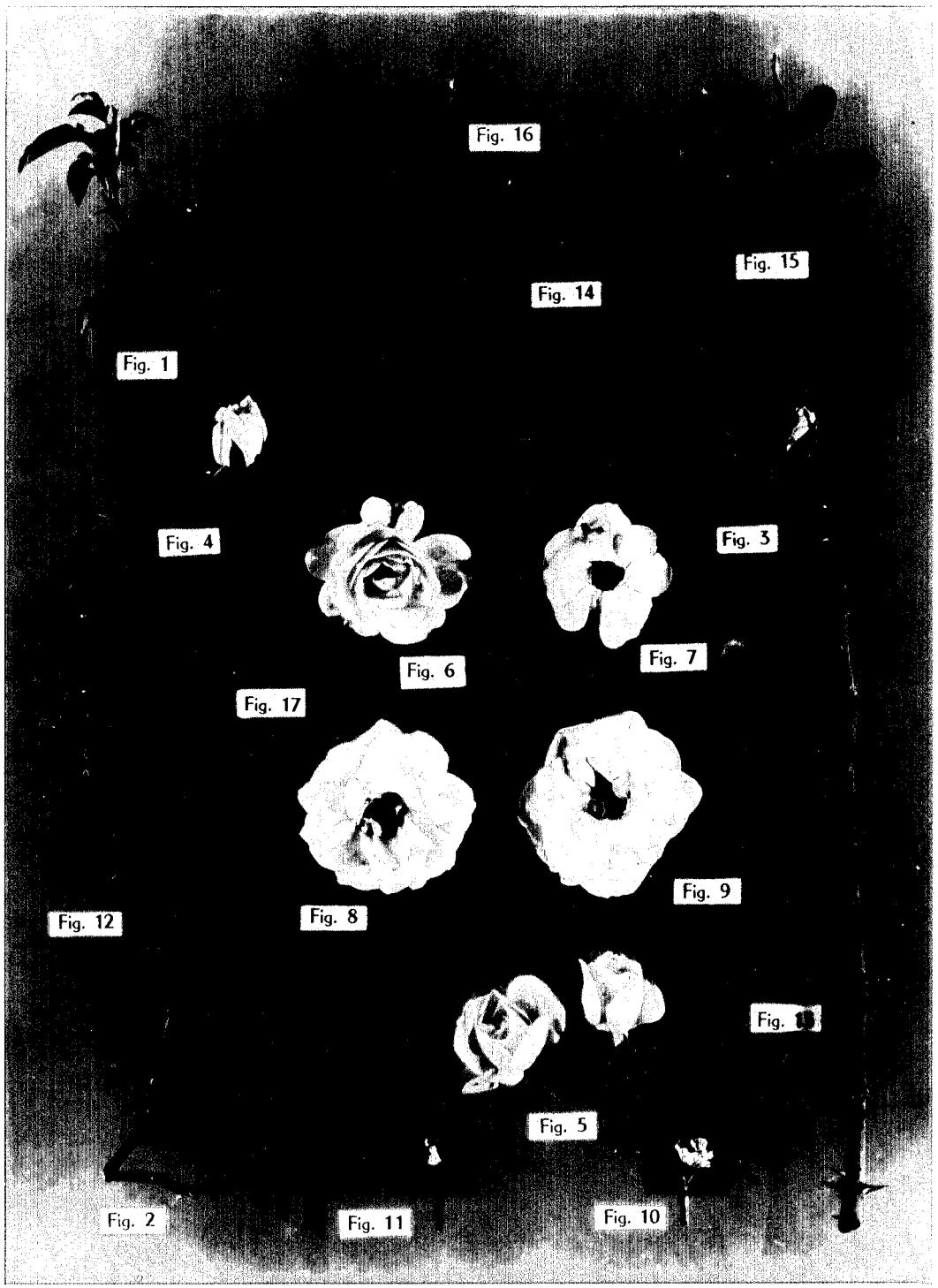
FIG. 1 illustrates a specimen of a young shoot.
FIG. 2 illustrates specimens of three floral buds before the opening of the sepals.
FIG. 3 illustrates specimens of two floral buds at the opening of the sepals.
FIG. 4 illustrates a specimen of a floral bud at the opening of the petals.
FIG. 5 illustrates specimens of two flowers in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils (sepals removed)
FIG. 11 illustrates a specimen of a floral receptacle showing the arrangement of the pistils (sepals and stamens removed)
FIG. 12 illustrates a specimen of a flowering stem.
FIG. 14 illustrates specimens of leaves with three leaflets with the upper surface being shown on the left and the under surface being shown on the right.
FIG. 15 illustrates specimens of leaves with five leaflets with the upper surface being shown on the right and the under surface being shown on the left.
FIG. 16 illustrates specimens of leaves with seven leaflets with the upper surface being shown on the bottom and the under surface being shown on the top.
FIG. 17 illustrates specimens of two fruits.

The chart used in the identification of the colors is that of The Royal Horticultural Society (R.H.S. Colour Chart). The terminology which precedes reference to the chart has been added to indicate the corresponding colors in common terms. The description is based on two year old specimens of the new variety during September while budded on *Rosa froebelli* understock and growing outdoors at LeCannet-des-Maures, Var, France.

Class: Miniature.

Plant:

*Height.*—Approximately 45 to 55 cm. on average.

*Habit.*—Bushy.

Branches:

*Color.*—Young Stems: light green, Yellow-Green Group 146C. Adult Wood: medium green, Yellow-Green Group 146B.

*Thorns.*—Size: small. Quantity: average. Color: pinkish on young leaves, and greenish pink changing to light brown on adult leaves.

Leaves:

*Petioles.*—Upper surface: striped reddish brown on young foliage and medium green on adult foliage with glandular edges. Under surface: light green with some grandular thorns.

*Stipules.*—Adnate, pectinate, wide and linear.

*Leaflets.*—Number: 3, 5, and 7. Shape: spear-shaped. Serration: simple and regular. Texture: leathery. General Appearance: very dense with bright foliage. Color (young foliage): Upper surface: dark green, Green Group 137A, and edged with reddish coloration. Under surface: light green, Green Group 137C, and more or less tinted with reddish coloration. Color (adult foliage): Upper surface: dark green, Yellow-Green Group 147A. Under surface: medium green, Yellow-Green Group 147B.

Inflorescence:

*Number of flowers.*—Approximately 1 to 6 per stem.

*Peduncle.*—Rigid, glandular and medium green in coloration, its length is approximately 2.3 to 3 cm. on average.

*Sepals.*—Upper surface: tomentose, and greenish in coloration. Under surface: medium green, the outside sepals have slightly appendiculate edges.

*Buds.*—Shape: oval. Length: approximately 2 cm. on average. Size: small. Color upon opening: Upper surface: light carmine rose, Red Group 52D. Under surface: light carmine rose, Red Group 52D, and tinted with carmine rose, Red Group 52C.

*Flower.*—Form: oval and fully double. Diameter: approximately 5 cm. on average. Color (when opening begins): Upper surface: carmine rose, Red Group 52D. Under surface: carmine rose, Red Group 52C. Color (when blooming): Upper surface: carmine rose, Red Group 52C. Under surface: carmine rose, Red Group 52C. Color (at end of opening): Upper surface: carmine rose, Red Group 52C, and changing to carmine rose, Red Group 52D on the outer petals. Under surface: carmine rose, Red Group 52C, and changing to white. Fragrance: slight. Lasting quality: long. Petal number: approximately 26 on average. Petal form: oval. Petal texture: firm. Petal drop: good. Anthers: normal, yellowish in coloration. Stamen number: approximately 80 to 85 on average. Filaments: greenish-straw colored and of irregular heights. Pistil number: approximately 38 to 42 on average. Stigmas: normal, straw colored. Styles: straw colored with a fuchsine top, more or less twisted, and of irregular heights. Receptacle: light green in coloration, and in longitudinal section are narrow and in the shape of a pitcher.

Development:

*Vegetation.*—Very vigorous.

*Blooming.*—Abundant and continuous.

*Aptitude to bear fruit.*—Good.

*Resistance to frost.*—Good.

*Resistance to disease.*—Very good.

I claim:

1. A new and distinct variety of Miniature rose plant characterized by the following combination of characteristics:

(a) forms in abundance on a continuous basis attractive fully double blossoms which are carmine rose in coloration, (b) exhibits a vigorous, compact and bushy growth habit, and (c) is not particularly affected by cryptogamic diseases; substantially as herein shown and described.

* * * * *